FR2 XR 4,547,315

United States Patent [19]

Rohr et al.

[11] Patent Number: 4,547,315

[45] Date of Patent: Oct. 15, 1985

[54] ALKYL ALPHA-CAMPHOLENATES AND DIHYDRO DERIVATIVES THEREOF AS ODORANTS AND FLAVORANTS

[75] Inventors: Martin Rohr, Glen Rock; Cormack Flynn, Ramsey, both of N.J.

[73] Assignee: Givaudan Corporation, Clifton, N.J.

[21] Appl. No.: 461,079

[22] Filed: Jan. 26, 1983

[51] Int. Cl.[4] .......... A61K 7/46; C11B 9/00

[52] U.S. Cl. .......... 252/522 R

[58] Field of Search .......... 252/522 R

[56] References Cited

PUBLICATIONS

Chemical Abstracts 90 61065c (1979).
Arctander, Perfume & Flavor Materials of Natural Origin, New Jersey Columns 168, 169, 326 to 328 (1960).
Chemical Abstracts 89 117519e (1978).
J. Cason et al., J. Org. Chem. 32, 575 (1967).
D. deRijke et al., Perfumer and Flavorist 7, 31 (1982).
M. Kagawa, Pharm. Bull (Tokyo) 4, 423 (1956).
H. Obermann, Dragoco Report 25, (3), 55 (1978).
F. Tiemann, Berichte 29, 3006-3014 (1896).
F. Mahla et al., Berichte 33, 1929-1932 (1900).

*Primary Examiner*—Helen M. S. Sneed
*Attorney, Agent, or Firm*—Robert F. Tavares

[57] ABSTRACT

The lower alkyl esters of α-campholenic acid and α-campholanic acid have organoleptic properties which make them useful for preparing fragrances and flavors.

8 Claims, No Drawings

ALKYL ALPHA-CAMPHOLENATES AND DIHYDRO DERIVATIVES THEREOF AS ODORANTS AND FLAVORANTS

BACKGROUND OF THE INVENTION

The art of creating flavors or fragrances involves blending a number of substances having individual characteristics to produce a composition which has the desired organoleptic effect. A successful product is not simply a combination of pleasant smelling or pleasant tasting materials; a successful product is one in which the individual character of each of the components is not readily perceived per se, but blends with each of the other odor or flavor notes to provide a single organoleptic impression.

To create this single organoleptic impression, the flavorist or perfumer uses a number of compounds which not only contribute their own characteristic odor or flavor to the blend, but which tie together the other materials used in the composition to form a more uniformly blended composition. This ability of a chemical to tie together individual contributions of the other materials is often described by the perfumer or flavorist as the ability to add "roundness" or "naturalness" to the composition. There is always a need for compounds which have this ability.

THE INVENTION

The present invention concerns fragrance and flavor compositions comprising the alkyl esters of formula I

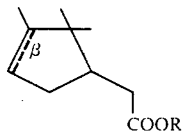

I wherein: the dotted line designated by $\beta$ is an optional bond, and R represents methyl, ethyl, propyl or butyl.

Propyl and butyl are to be understood as encompassing both the straight chain and branched isomers. The compounds of formula I have organoleptic properties that make them useful in fragrance and flavor compositions.

The compounds of formula I are derivatives of $\alpha$-campholenic acid. The ethyl and methyl esters are reported in the prior art; see F. Mahla et al. Berichte 33, 1929–1932 (1900); see H. Obermann, Dragoco Report 3,55 (1978); M. Kagawa, Pharm. Bull. (Tokyo) 4, 423 (1956); and J. Cason et al., J. Org. Chem. 32, 575 (1967). The other compounds of this invention are novel.

The compounds of this invention may be prepared by general methods known in the art for preparing esters. A preferred method for their preparation is described herein.

DESCRIPTION OF THE PREFERRED EMBODIMENTS

A number of alkyl $\alpha$-campholenates and $\alpha$-campholanates of formula I are listed in Table I along with a description of their organoleptic properties.

TABLE I

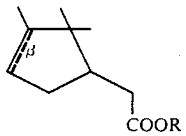

I

| R | $\beta$-bond | Odor Description | Flavor Description |
|---|---|---|---|
| $CH_3$ | double | fatty, green, fruity, floral | fruity, apple, woody |
| $C_2H_5$ | double | fruity, berry, blueberry, apple, winy | sweet, fruity, vegetative, blueberry |
| n-$C_3H_7$ | double | fruity, apple, woody | weak, fruity |
| n-$C_4H_9$ | double | fruity, woody, resinous | weak, fruity, berry |
| iso-$C_4H_9$ | double | fruity, peach | weak, fruity, berry |
| $CH_3$ | single | fruity, green, fatty floral | dry, woody, herbaceous |
| $C_2H_5$ | single | fruity, berry, blueberry, apple, winy | sweet, herbaceous, woody, fruity |
| n-$C_3H_7$ | single | fruity, fatty | sweet, fruity, berry character |
| n-$C_4H_9$ | single | weak, waxy | weak, herbaceous, woody |

The esters of this invention could be prepared by a chemist using methodology known in the art. A preferred method for preparing the $\alpha$-campholenic acid esters involves the oxidation of $\alpha$-campholenic aldehyde (e.g. via Jones oxidation) to $\alpha$-campholenic acid and the subsequent esterification of the acid using the appropriate alcohol and an acid catalyst. These alkyl $\alpha$-campholenates can be hydrogenated to the corresponding alkyl $\alpha$-campholanates in the presence of a metal catalyst (e.g. 5% Pd/C). These reactions are represented as follows.

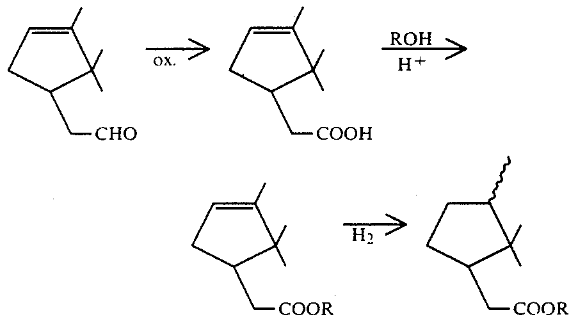

The compounds of formula I have organoleptic properties that make them useful in fragrance and flavor compositions, especially flavors of the fruity type and fragrances of the fruity and floral types. Each compound has its own unique fragrance and flavor properties and each is useful to add "roundness" or "naturalness" to a variety of compositions. The ethyl esters are definitely preferred for use in both flavors and fragrances because of their distinct superiority to the others. They have an outstanding ability to provide "roundness" and "naturalness" to flavors and fragrances. These ethyl esters have a strong berry-like character reminiscent of blueberry. They are more berry-like, more rounded and generally more preferred than the methyl esters. They are more intense, more natural and more berry-like than the propyl and butyl analogs.

While the compounds of formula I can be used to contribute interesting fragrance and/or flavor properties to a composition, they are valuable, particularly the ethyl esters, for blending diverse notes in a flavor or fragrance composition. By the blending of diverse notes we refer to the situation wherein the practitioner has made a basic blend of ingredients, each of which contributes its own character, and finds that a number of different impressions are recognized. In order to achieve the goal of a single and uniform sensory impression, a modifier must be added to bring together these diverse organoleptic impressions into a blended composition which creates a single and uniform impression.

A number of examples have been provided to illustrate the use of the ethyl esters to blend fragrance compositions and add roundness and naturalness. For example, in floral compositions the addition of an ethyl ester tended to fill the gap between the ionones and the natural florals to provide a more natural, more rounded and more uniform floral impression. In an iris base the ionone and jasmine aromatic notes were blended and a fragrance composition which was more uniform, more natural and more reminiscent of the odor produced by the flower was produced by adding the ethyl esters. When used in a rose base, the ethyl esters provided fruity nuances which blended with floral notes to provide a more natural and better blended impression which was more reminiscent of the odor produced by the flower itself. In each instance, the fragrance with the ethyl esters was better blended, rounder and more natural.

This ability to blend was perhaps best illustrated in a soap fragrance. A typical soap fragrance normally contains high impact chemicals having odors which, because of their intensity, are often described as harsh. Addition of the ethyl ester softened the harsh impression produced by the high impact chemicals and imparted a natural fruity odor which blended with and emphasized the floral notes of the fragrance.

Effects of a similar nature are illustrated in flavor compositions. Not only berry flavors, but non-berry flavors such as a vanilla were found to be better blended, more uniform and more natural upon the addition of the ethyl esters. A vanilla was found to be creamier, richer and more natural in vanilla character. Similarly a blueberry formulation was found to have more body, sweetness and be more reminiscent of a natural blueberry. Similar effects were noted in a grape drink.

When used in smoking tobacco, the ethyl esters improved the quality of the smoking by improving the sensation in the mouth (mouth feel). The smoking was described as being smoother and as leaving the mouth with an increased and desirable sensation of moistness.

Because of their ability to unite and blend a number of diverse and different notes, the compounds of this invention can be used in a wide variety of fragrance types and their use is limited only by the imagination and skill of the perfumer. It appears, however, that these chemicals are particularly suitable for use in floral and fruity type compositions.

Depending on the fragrance composition and the compound used, concentrations as low as 0.1% can be used for the preferred ethyl esters. A preferred range for the ethyl esters would be from 0.5% to 50%. The lower range (1% to 2%) is preferred when the compounds are principally used to modify and blend diverse odor notes while the upper range, anywhere from 2% to 50%, is preferred when the compound is to serve as a major odor contributor. Higher concentrations, even as high as 95% may be used to produce special effects.

Fragrance compositions containing the compounds of the invention can be used as odorant bases for the preparation of perfumes and toilet waters by adding the usual alcoholic and aqueous dilutents thereto. Approximately 15–20% by weight of base would be used for perfumes and approximately 3–5% by weight would be used for toilet waters.

Similarly, the fragrance compositions can be used to odorize soaps, detergents, cosmetics, or the like. In these instances, a base concentration of from about 0.5% to about 2% by weight can be used.

The esters of this invention can be added to foodstuffs, drinks and/or luxury consumables per se or they can be used to prepare flavoring compositions which are to be added thereto. A flavoring composition is comprised of a mixture of flavor imparting substances and perhaps a diluent, carrier and/or other adjuvants. These flavoring mixtures are then used to impart flavors to foodstuffs. Depending on the ester to be used, the flavor desired and the foodstuff to be flavored, the amount of the ester of formula I used in the flavor composition can vary over a wide range. The compounds of formula I may be as little as 0.001% of the flavor imparting substances present. In most applications, however, the ester would be at a level of about 0.01% to 1.0% of the flavor imparting substances present. Levels as high as 10% may be desirable in some applications and, as has been mentioned above, the ester itself may be added to foodstuffs to improve, enhance and/or alter the flavor.

The flavoring substances described above are added to or incorporated into the foodstuffs to be flavored using methods well known in the art. The amount of flavoring composition used will depend on the flavor to be imparted and the foodstuff flavored. The amount of the compounds of formula I used in the foodstuffs can be as little as 0.01 parts per million to as much as 100 parts per million. In most foodstuffs, the level of ester used will be in the range of about 0.1 parts per million to about 10 parts per million.

Such foodstuffs are intended to include, but are not limited to chewing gums, candies, jellies, gelatins, desserts, liquors, yogurts, teas, and the like.

The use of the compounds of formula I in tobacco or tobacco products is intended to include, but not be limited to, tobacco itself, tobacco by-products such as reconstituted and homogenized leaf and stem, tobacco surrogates such as lettuce and cabbage leaf, tobacco processing materials such as paper, filters, etc., and flavoring substance compositions used for tobacco products.

In flavoring tobacco or tobacco products, the preferred range would be between 100 ppm and 250 ppm of the tobacco or tobacco substitute used with 175 ppm to 225 ppm being especially preferred.

The claims are to be understood as not encompassing the use of natural materials which may contain an ester of this invention along with many other compounds of said natural materials and which have not been processed for the purpose of increasing the concentration of the esters of this invention to a point where the processed material can be used as a substitute for said esters contained therein.

ILLUSTRATION OF THE PREFERRED EMBODIMENTS

The following examples are provided to illustrate further the practice of the present invention and should not be construed as limiting.

Gas-liquid chromatography was used to analyze the products. Weights are given in grams.

EXAMPLE I

Preparation of alkyl esters of α-campholenic acid

A. 2,2,3-Trimethyl-3-cyclopentene-1-acetic acid (α-campholenic acid).

A solution was made of α-campholenic aldehyde (200 g) in acetone (2 liters) and cooled to 0° C. Jones reagent was prepared from 115 ml conc. sulfuric acid, 500 ml water and 134 g of chromium (VI) oxide. The reagent (400 ml) was added to the solution at 0° C. over a period of 30 minutes. After an additional 15 minutes at 0° C. the acetone was removed by decantation and the residual chromium salts were washed with an additional 200 ml acetone. The combined acetone solution was concentrated to 1 liter, diluted with 10% aqueous sodium hydroxide (1 liter) and washed with $CH_2Cl_2$(2×1 liter). The aqueous phase was acidified with 25% sulfuric acid and extracted with $CH_2Cl_2$ (2×1 liter). Concentration of the $CH_2Cl_2$ solution yielded an oil (145 g) which was distilled under reduced pressure to give 116 g of a yellowish liquid; bp 121° C. @ 2.2 mm Hg; analysis: 98% (CW 20M fused silica column, 180° C.) α-campholenic acid.

B. 2,2,3-Trimethyl-3-cyclopentene-1-acetic acid ethyl ester (Ethyl α-campholenate).

A solution of α-campholenic acid (100 g) and p-toluene-sulfonic acid (2 g) in ethanol (3 liters) was kept at reflux (78° C.) for 3 hours. The alcohol was then removed, the residue taken up in $CH_2Cl_2$ (1.5 liters) and the solution extracted with ice cold 5% aqueous sodium hydroxide (2×500 ml) and water (500 ml). Concentration of the $CH_2Cl_2$ solution gave a crude product (81 g) which was distilled through a 9" glass packed column to give 75 g of a colorless liquid; bp 90° C. @ 4,8 mm Hg; analysis: 97% (CW 20M fused silica column, 120° C.) ethyl α-campholenate.

The corresponding methyl, n-propyl, n-butyl and isobutyl α-campholenates were prepared from the appropriate alcohol in a manner similar to that described for the ethyl ester. The structure of each was confirmed by mass spectroscopy, infrared spectroscopy and proton magnetic resonance.

EXAMPLE II

Preparation of alkyl esters of α-campholanic acid

A. 2,2,3-Trimethylcyclopentane-1-acetic acid ethyl ester (Ethyl-α-campholanate).

Ethyl α-campholenate (5.0 g), prepared as described in Example I, was hydrogenated in 50 ml of ethanol at 50 psi at room temperature in the presence of 5% palladium on carbon (0.1 g) using a Parr hydrogenator. When hydrogen uptake ceased, the mixture was filtered and concentrated. The resultant crude product was purified by bulb to bulb distillation at 100° C. @ 0.3 mm Hg to yield 4.8 g of a colorless liquid; analysis 98% (CW20M fused silica column, 55°-190° C.; 10° C./min.) ethyl-α-campholanate as a mixture of stereoisomers.

The corresponding methyl, n-propyl and n-butyl α-campholanates were prepared from the corresponding alkyl α-campholenates in a manner similar to that described for the ethyl ester. The structure of each was confirmed by mass spectroscopy, infrared spectroscopy and proton magnetic resonance.

EXAMPLE III

Use of ethyl α-campholenate as an odorant

A. Iris Base

| Components | Parts by Weight |
|---|---|
| ISORALDEINE ® -70 (methylionone mixture) | 100 |
| α-Ionone | 200 |
| Irone Alpha, refined (6-methylionone) | 10 |
| Cinnamon Leaf Oil | 15 |
| Heliotropin | 40 |
| Ylang Oil (Bourbon) | 20 |
| Jasmin Oil (Synthetic) | 25 |
| Methyl Octine Carbonate | 2 |
| Iris Aldehyde (2-nonen-1-al), 10% in dipropylene glycol | 2 |
| Phenyl Ethyl Alcohol | 50 |
| Coumarin | 15 |
| Citronellol | 50 |
| Benzyl Acetate | 10 |
| Total | 539 |

The Iris base formulated as above is found lacking in unity; the odors of Isoraldeine ®, α-ionone and irone-alpha are not fully integrated with the odors of the rose and jasmin aromatics. The resulting fragrance is dominated by the odor of ionones which give the base a synthetic quality. The addition of 200 parts (27%) of ethyl α-campholenate unites the ionones into a more natural, full bodied and complete floral fragrance. Similar effects can be achieved by the addition of like amounts of ethyl α-campholanate.

B. Rose Base

| Components | Parts by Weight |
|---|---|
| Phenyl Ethyl Alcohol | 350 |
| Citronellol | 200 |
| Geraniol | 300 |
| Viridine TM (phenylacetaldehyde dimethyl acetal) | 5 |
| Guaiacwood concrete | 20 |
| Total | 875 |

The Rose base as formulated above is found thin and lacking in the fruity odors inherent in a natural rose fragrance.

The addition of 10 parts (1.1%) of ethyl α-campholenate to the base adds a fruity nuance which blends into the floral notes and makes the base more natural and therefore more appealing.

Similar effects can be achieved by the addition of like amounts of ethyl α-campholanate.

C. Soap Fragrance

| Components | Parts by Weight |
|---|---|
| Terpinyl Acetate | 40 |
| Bergamyl Acetate TM (pseudo-linalyl acetate) | 15 |
| LEMONILE ® (3,7-dimethyl-2,6-nonadienenitrile) | 1 |
| Linalool (Synthetic) | 20 |
| Ylang Oil (Synthetic) | 15 |
| Benzyl Acetate | 20 |
| Geraniol | 25 |
| Phenyl Ethyl Alcohol | 25 |
| Methyl Phenyl Carbinyl Acetate | 6 |
| Eugenol | 20 |

-continued

| Components | Parts by Weight |
|---|---|
| Benzyl Salicylate | 150 |
| SANDALORE ® [5-(2,2,3-trimethyl-cyclopent-3-en-1-yl)3-methylpentan-2-ol] | 8 |
| Aldehyde C-11, Undecylenic | 3 |
| Gamma-Undecalactone | 3 |
| LILIAL ® (p-t-butyl-α-methylhydrocinnamaldehyde) | 50 |
| Cinnamon Leaf Oil | 2 |
| Ethyl Vanillin | 2 |
| β-Naphthol Ethyl Ether | 10 |
| Thibetolide TM (pentadecanolide) | 45 |
| Cedartone TM V (acetylcedrene) | 30 |
| p-tert-Butylcyclohexyl Acetate | 30 |
| Phenyl Acetic Acid, 10% in dipropylene glycol | 2 |
| Costus Oil (synthetic) | 2 |
| Cumin Oil, 10% in dipropylene glycol | 5 |
| Gamma-Nonalactone | 2 |
| Total | 531 |

The soap fragrance, as formulated above and which is in the direction of Carnation-woody-musky, was found to be harsh and somewhat uneven. The floral character of the fragrance was somewhat subdued. The addition of 20 parts (3.6%) of ethyl α-campholenate softened the harshness adding a natural fruity note which accentuated the floral character.

Similar results can be achieved with the use of ethyl α-campholanate.

EXAMPLE IV

Use of ethyl α-campholenate as a flavorant

A. Artificial Vanilla Flavor

| Components | Parts by Weight |
|---|---|
| Vanillin | 5.0 |
| Heliotropin | 0.2 |
| Veratraldehyde | 0.3 |
| Benzodihydropyrone | 0.2 |
| Ethyl Vanillin | 0.3 |
| Ethanol (95%) | 50.0 |
| Water (distilled) | 44.0 |
| Total | 100.0 |

A taste solution was prepared by adding 0.1 g of the above artificial vanilla flavor to a solution of 100 g of sucrose in 900 g of distilled water. To 100 g of the artificial vanilla flavored taste solution was added 0.1 g of a 0.01% solution of ethyl α-campholenate in ethanol (0.1 ppm in the finished drink). A bench panel of four tasters compared the solution containing the additive to the untreated solution. All preferred the artificial vanilla containing the additive stating that it was creamier, richer in vanilla character, more natural and closer to pure vanilla extract.

B. Artificial Blueberry Flavor

| Components | Parts by Weight |
|---|---|
| Ethyl Acetate | 50.0 |
| cis-3-Hexenol | 10.0 |
| Amyl Butyrate | 5.0 |
| Ethyl Isovalerate | 20.0 |
| Linalool | 10.0 |
| Vanillin | 5.0 |
| Total | 100.0 |

A blueberry flavor solution was prepared by adding 1.0 g of the above blueberry flavor concentrate to 99.0 g of 95% ethanol. A blueberry flavored drink was prepared by adding 2.0 g of the above blueberry flavor solution to 100 g sucrose and 0.5 g malic acid in 899.3 g distilled water. To 500 g of the blueberry flavored drink was added 0.1 g of a 1.0% solution of ethyl α-campholenate in ethanol (approximately 2 ppm in the finished drink). A bench panel of four tasters compared the solution containing the additive to the untreated solution. All preferred the blueberry flavored drink containing the additive stating that it had more body, sweetness and a more natural blueberry flavor.

C. Artificial Grape Flavor

| Components | Parts by Weight |
|---|---|
| Methyl Anthranilate | 55.0 |
| Ethyl Anthranilate | 15.0 |
| Ethyl Butyrate | 2.0 |
| Triethyl Citrate | 20.0 |
| Ethyl Acetate | 0.4 |
| Geranyl Acetate | 0.2 |
| Amyl Acetate | 0.1 |
| Geranyl Propionate | 0.2 |
| Ethyl Heptanoate | 2.0 |
| Ethyl Oenanthate | 3.5 |
| Ethyl Pelargonate | 0.5 |
| Ethyl Caproate | 0.2 |
| α-Ionone | 0.2 |
| Amyl Butyrate | 0.2 |
| Ethyl Vanillin | 0.3 |
| Ethyl Propionate | 0.2 |
| Total | 100.0 |

A grape flavor solution was prepared by adding 1.0 g of the above grape flavor concentrate to 99.0 g of 95% ethanol. A grape flavored drink was prepared by adding 2.0 g of the above grape flavor solution to 120 g sucrose and 1.0 g tartaric acid in 877 g distilled water. To 500 g of the grape flavored drink was added 0.05 g of a 1.0% solution of ethyl α-campholenate in ethanol (approximately 1 ppm in the finished drink). A bench panel of four tasters compared the solution containing the additive to the untreated solution. All tasters preferred the grape flavored drink containing the additive stating that it was more natural tasting, well-rounded and more grape-like in character.

D. Gelatin Mix

| Components | Parts by Weight |
|---|---|
| Gelatin 250 bloom | 6.50 |
| Sucrose | 75.00 |
| Adipic Acid | 2.50 |
| Sodium Citrate | 0.85 |
| Salt | 0.15 |
| Total | 85.00 |

The above components were combined and dissolved in 415 g of hot water. To this gelatin mix was added 1.0 g of the grape flavored solution as prepared in section C above. To 100 g of the grape flavored gelatin mix was added 0.02 g of a 1.0% solution of ethyl α-campholenate in ethanol (approximately 2 ppm in gelatin mix). A bench panel of four tasters compared the grape flavored gelatin mix with and without the additive and found the gelatin mix with the additive was more natural, well-rounded and contained a preferred grape flavoring.

E. Commercial Application—Blueberry Pie Filling

Ethyl α-campholenate was added to commercially available blueberry pie filling at a level of 1 ppm. A bench panel of four tasters compared the treated pie filling containing the additive with the untreated filling. All preferred the filling containing the additive stating that it had more aroma and greater blueberry character.

F. Tobacco Product

A standard cigarette blend was prepared as described below:

| Components | Parts by Weight |
|---|---|
| Bright Tobacco | 55 |
| Burley Tobacco | 25 |
| Expanded Stems | 5 |
| Reconstituted Leaf | 15 |
| Total | 100 |

Ethyl α-campholenate at 200 ppm was added to cigarettes prepared from the above tobacco blend. The cigarettes with and without the additive were evaluated by smoking. The cigarettes with the additive were found to have enhancement of mouth feel (fullness), smoother mainstream and increased moistness of the mouth.

We claim:

1. A fragrance composition comprising an olfactorily effective amount of a compound of the formula

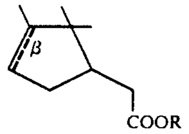

I wherein:

R represents methyl, ethyl, propyl or butyl, and the dotted line designated by β is an optional bond, and at least one other olfactory agent.

2. A composition according to claim 1 wherein the optional bond represented by the dotted line is present.

3. A composition according to claim 2 wherein the compound is 2,2,3-trimethyl-3-cyclopentene-1-acetic acid ethyl ester.

4. A composition according to claim 1 wherein the optional bond represented by the dotted line is absent.

5. A composition according to claim 4 wherein the compound is 2,2,3-trimethylcyclopentane-1-acetic acid ethyl ester.

6. A method for improving the odor of a fragrance composition which comprises adding thereto an olfactorily effective amount of a compound of the formula

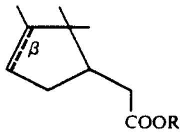

I wherein:

R represents methyl, ethyl, propyl or butyl, and the dotted line designated by β is an optional bond.

7. The method of claim 6 wherein 2,2,3-trimethyl-3-cyclopentene-1-acetic acid ethyl ester is added.

8. The method of claim 6 wherein 2,2,3-trimethylcyclopentane-1-acetic acid ethyl ester is added.

* * * * *